United States Patent [19]
Baumann et al.

[11] Patent Number: 5,463,467
[45] Date of Patent: Oct. 31, 1995

[54] LIGHT SOURCE PULSED WITH IRREGULAR PULSE SEQUENCE IN ANALOG PHOTOMETRIC SIGNAL EVALUATION FOR A TEST CARRIER ANALYSIS SYSTEM

[75] Inventors: Edgar Baumann, Mannheim; Wolfgang Obermeier; Karl Werner, both of Heidelberg, all of Germany

[73] Assignee: Boehringer Mannheim GmbH, Mannheim, Germany

[21] Appl. No.: 266,378

[22] Filed: Jun. 27, 1994

[30] Foreign Application Priority Data

Jun. 29, 1993 [DE] Germany ............ 43 21 548.3

[51] Int. Cl.$^6$ ............... G01N 21/47; G01J 1/44
[52] U.S. Cl. ............... 356/446; 356/226
[58] Field of Search ............... 356/445–448, 356/217, 215, 226, 233

[56] References Cited

U.S. PATENT DOCUMENTS

| | | | |
|---|---|---|---|
| 3,684,378 | 8/1972 | Lord | 356/447 |
| 3,874,799 | 4/1975 | Isaacs et al. | 356/226 |
| 4,061,925 | 12/1977 | Van der Gaag et al. | 250/553 |
| 4,066,964 | 1/1978 | Costanza et al. | 375/38 |
| 4,201,472 | 5/1980 | Maeda | 356/226 |
| 4,320,970 | 3/1982 | Dowben et al. | 356/317 |
| 4,553,848 | 11/1985 | Rösicke et al. | 356/448 |
| 4,568,966 | 2/1986 | Lippel | 358/13 |
| 5,066,859 | 11/1991 | Karkar et al. | 356/41 |
| 5,177,565 | 1/1993 | Stoughton | 356/446 |
| 5,249,027 | 9/1993 | Mathur et al. | 356/1 |

FOREIGN PATENT DOCUMENTS

| | | |
|---|---|---|
| 0256806 | 2/1988 | European Pat. Off. . |
| 0497397A1 | 8/1992 | European Pat. Off. . |
| 2902776 | 8/1979 | Germany . |
| 3538472A1 | 4/1987 | Germany . |
| 8907967.1 | 10/1989 | Germany . |
| 3833303A1 | 4/1990 | Germany . |
| 4140069C1 | 11/1992 | Germany . |
| 4119406A1 | 12/1992 | Germany . |
| WO83/00926 | 3/1983 | WIPO . |

OTHER PUBLICATIONS

"Erzeugung von Pseudo–Zufallsfolgen mit binären Schieberegistern" (Production of pseudo–random sequences with binary shift registers), published in Electronik, special edition 209, Franzis Verlag, p. 93.

Primary Examiner—Richard A. Rosenberger
Assistant Examiner—Jason D. Eisenberg
Attorney, Agent, or Firm—Nikaido, Marmelstein, Murray & Oram

[57] ABSTRACT

Method of detecting and evaluating analog photometric signals in a test carrier analysis system, and apparatus for carrying out the method. The test field of a test carrier is irradiated by a light source clocked in light-dark phases. The reflected light is detected by a measurement receiver over a measurement period having several light-dark phases, and integrated. An effective suppression of stray and secondary light, which permits measurement even without the hitherto conventional shielding from ambient light, is achieved by a method in which the sequence of the light and dark phases integrated over the measurement period is irregular in such a way that the Fourier-transformed frequency spectrum includes a large number of different frequencies. Each individual frequency therefore makes only a small contribution to the measurement result.

37 Claims, 7 Drawing Sheets

LIGHT SOURCE PULSED WITH IRREGULAR PULSE SEQUENCE IN ANALOG PHOTOMETRIC SIGNAL EVALUATION FOR A TEST CARRIER ANALYSIS SYSTEM

BACKGROUND OF THE INVENTION

1. Field of the Invention

The invention relates to a method of detecting and evaluating analog photometric signals in a test carrier analysis system, wherein the test field of a test carrier is irradiated by a light source clocked in light-dark phases, the light reflected by the test field is detected by a measurement receiver and its measured value is passed to a measurement integration and digitalization circuit for evaluation, and wherein, over a measurement period comprising several light and dark phases of the clocked light source, the measured value is integrated over at least part of each light phase and over at least part of each dark phase, and a total integrated value is formed from the integrals of the light and dark phases in the measurement integration and digitalization circuit.

The invention further relates to an arrangement for carrying out the method.

2. Description of the Related Art

Test carrier analysis systems are increasingly used for the analysis of fluids, especially body fluids, such as blood or urine, for the purpose of medical examination. These systems consist essentially of evaluation apparatuses and the appropriately designed test carriers.

The test carriers frequently take the form of test strips whose test fields are conventionally made up of a base layer and at least one test layer arranged thereon. The test layer contains one or more reagents. When a sample, for example a body fluid, is applied to the test layer, a chemical reaction takes place with components of the sample and leads to a detectable change in the test field, especially to a color change in a detection layer. This change can be evaluated for quantitative analysis by means of suitable methods and corresponding apparatuses.

Thus, for example, after the reaction has taken place, a reflection-photometric measurement by means of the evaluation apparatus can be used to infer, from the diffuse reflectivity of the test field, the concentration of that component of a body fluid which is to be determined. In other cases, the desired analysis result can be derived from the change in reflectivity over time.

Particularly stringent accuracy demands are made on the detection and evaluation of the photometric signals in order to detect the very small measurement currents or measurement voltages with sufficient resolution for determination of the generally small change in reflectivity and to permit quantitative analysis. On the other hand there is a large number of sources of interference. These are on the one hand the known problems associated with evaluation electronics for the detection of very small signals, such as amplifier drift, superimposed direct voltages, high-frequency noise voltages, low-frequency alternating and ripple voltages, due especially to pick-ups at mains frequency, amplifier input currents and creeping or residual currents of various kinds.

In addition there are the typical interferences associated with optical measurements, caused by secondary and stray light in the form of disturbing external light. These include both relatively constant external light components and typical interferences from mains-operated light sources working at the conventional mains frequency of 50 Hz or 60 Hz.

Hitherto, test carrier evaluation apparatuses have normally been constructed so that, to avoid the abovementioned disturbing external light components, external light has been prevented as far as possible from entering the measurement area of the apparatus, where the test field, the clocked light source and the measurement receiver are located during the measurement. For this purpose, the test carrier was inserted, for example, in a narrow channel. In other apparatuses, the test carrier holder for accommodating the test carrier during the measurement was located inside a lightproof housing with a flap, which had to be opened for insertion of the test strip and closed for the measurement.

These known light-shielding measures have disadvantages associated with them. Narrow channels easily become soiled when the test carrier, for example a blood sample, is inserted. In the second case, the construction and manufacturing costs are increased by the need for a flap. Moreover, it has been found that the flap is frequently a cause of operating errors if it is not completely closed or is opened too early. It has to be taken into consideration here that test strip evaluation apparatuses are used principally by diabetics for self-determination of their glucose levels. However, the nature of their illness is such that diabetics often have limited manual dexterity or impaired vision.

For larger analysis apparatuses, including in some cases those which form part of a test carrier analysis system, proposals have already been made for the additional electronic suppression of the interferences caused by disturbing external light. Here the light source is clocked in light and dark phases. The signals from the measurement receiver are then evaluated over part of both the light phase and the dark phase, after which subtraction of the result of the dark phase from that of the light phase makes it possible substantially to eliminate interferences which make additive contributions to the measurement signal and change slowly in relation to the clock frequency of the light source.

Suitable methods of suppressing high-frequency interferences are those in which the signal from the measurement receiver is integrated over a certain measurement period. This substantially suppresses interferences whose frequencies are much greater than the reciprocal integration time.

German patent specification 28 14 358 discloses a method and a corresponding arrangement which combine these two measures. Here a measurement receiver is irradiated by the clocked light source and the signals are integrated over part of both the light phase and the dark phase. In this known method, the signal from the measurement receiver is evaluated over both the light phase and the dark phase and the two digitalized results are then subtracted from one another to give a corrected measured value.

European patent specification 0 075 767 proposes a method and a corresponding arrangement in which measuring errors of the abovementioned type are suppressed in a simple manner and with low construction costs, the resolution and accuracy being high. Said patent specification discloses a method of the type indicated at the outset, where integration over several consecutive light and dark phases is carried out without intermediate digitalization, thereby realizing a long integration time at a nevertheless relatively high clock frequency of the light source. This largely eliminates on the one hand high-frequency interferences which are still of relatively low frequency because of the long integration time, and on the other hand direct voltage components which also change relatively rapidly because of the relatively high clock frequency.

SUMMARY OF THE INVENTION

The object of the invention, in the light of the state of the art, is to provide a method of detecting and evaluating analog photometric signals in a test carrier analysis system, and an arrangement for carrying out the method, wherein the elimination of the disturbing external light components is improved in such a way that the measurement can also be made with a test carrier analysis system without any kind of shielding from sources of disturbing external light at normal ambient luminosity in an open arrangement.

To achieve this object with a method of the type indicated at the outset, the sequence of the light and dark phases integrated over the measurement period is irregular in such a way that the frequency spectrum obtainable therefrom by Fourier transformation comprises a large number of different frequencies. Within the framework of the invention, it has been recognized that the suppression of disturbing external light associated with a regular sequence of the light and dark phases is inadequate. This is attributable to the fact that the disturbing external light sometimes contains problematical sources of light which are not frequency-stable, examples being camping lights or stroboscopic lamps. Moreover, frequencies synchronous with the frequency of the uniformly clocked light source, or integral multiples thereof, cannot be completely avoided.

In the method according to the invention, the pulse sequence of the light and dark phases corresponds to a broad frequency spectrum. Accordingly, each individual frequency makes only a small contribution to the measurement result, so corresponding interfering frequencies can also make only a fractional error contribution to the falsification of the measurement result. This method achieves an extremely good suppression of the disturbing external light component, enabling the measurement to be made totally without light shielding in ambient light.

In a first advantageous embodiment, the sequence of the light and dark phases is generated by means of a random generator. Although it is possible to use a true random generator, the electronic realization is technically complicated, especially as it is necessary to ensure that an integration time of equal length is realized for each of the light and dark phases overall.

Therefore, the sequence of the light and dark phases is preferably generated as a predetermined pseudo-random sequence. It can be realized for example by means of a preset retroactive shift register, optionally in conjunction with a downstream modulator. This is illustrated in more detail for example in the article "Erzeugung von Pseudo-Zufallsfolgen mit binären Schieberegistern" ("Production of pseudo-random sequences with binary shift registers"), published in "Elektronik" special edition 209, "Elektronik Arbeitsblätter" Franzis Verlag, p 93 et seq Advantageously, to give the total integrated value, the measured value from the measurement receiver is integrated not just over one pseudo-random sequence but over other identical pseudo-random sequences as well. Repetition of the pseudo-random sequence one or more times improves the signal-to-noise ratio.

In a further preferred embodiment of the method according to the invention, at the beginning of each of the light and dark phases, the measured value from the receiver is not integrated over a delay time. In this way, overshoot effects at the beginning of a light phase, relaxation effects at the beginning of a dark phase and other transient processes are not included in the integration and do not therefore make any error contribution to the measurement result.

According to one advantageous feature, the integration over the integrated parts of the light phases and the integrated parts of the dark phases is carried out in each case in several consecutive sampling steps. This procedure has the advantage that the method can be implemented using switched capacitor technology.

Of particular importance for the method according to the invention is the fact that the Fourier-transformed frequency spectrum comprises a large number of different frequencies. The greater the frequency range over which the frequencies are distributed, and the greater the number of different frequencies which make a substantial contribution to the overall intensity, the better is the suppression of the influence of sources of disturbing external light on the measurement. In other words, the discrete Fourier-transformed frequency spectrum should approximate as far as possible to the theoretically ideal but practically unachievable limiting case of a continuous frequency spectrum having a constant intensity and the broadest possible band (a "white" spectrum which at most displays so-called notch frequencies in the case of specific, commonly occurring interfering frequencies such as the mains frequency of 50 Hz or 60 Hz).

The arrangement according to the invention for carrying out the method has the following elements: a light source for irradiating that test field of a test carrier which is to be examined; a triggering device for triggering the light source, clocked in light-dark phases; a pulse sequence generator for generating the pulse sequence for the triggering device; a measurement receiver for picking up the light reflected by the test field; and a measurement integration and digitalization circuit to which the measured value from the measurement receiver is passed for measurement, integration and digitalization. This circuit comprises a preamplifier for amplifying the signals from the measurement receiver and a relay multiplication stage for producing a correlation signal. By means of the multiplication stage the output signal from the preamplifier is provided with opposite polarity signs for the duration of the measurement period over at least part of a light phase and over at least part of a dark phase. The circuit also comprises an analog-to-digital converter for integrating the correlation signal over the measurement period so that the analog integrated measured value obtained over the integrated part of the dark phase is subtracted from the analog integrated measured value obtained over the integrated part of the light phase to give a total analog integrated value, and for conversion to a measurement event number, and a control circuit for controlling the course of the measurement. The pulse sequence generator here is a random sequence generator generating an irregular pulse sequence.

BRIEF DESCRIPTION OF THE DRAWINGS

The invention is explained in more detail below with the aid of embodiments represented diagrammatically in the Figures.

DETAILED DESCRIPTION OF THE PREFERRED EMBODIMENTS

Figure 1:
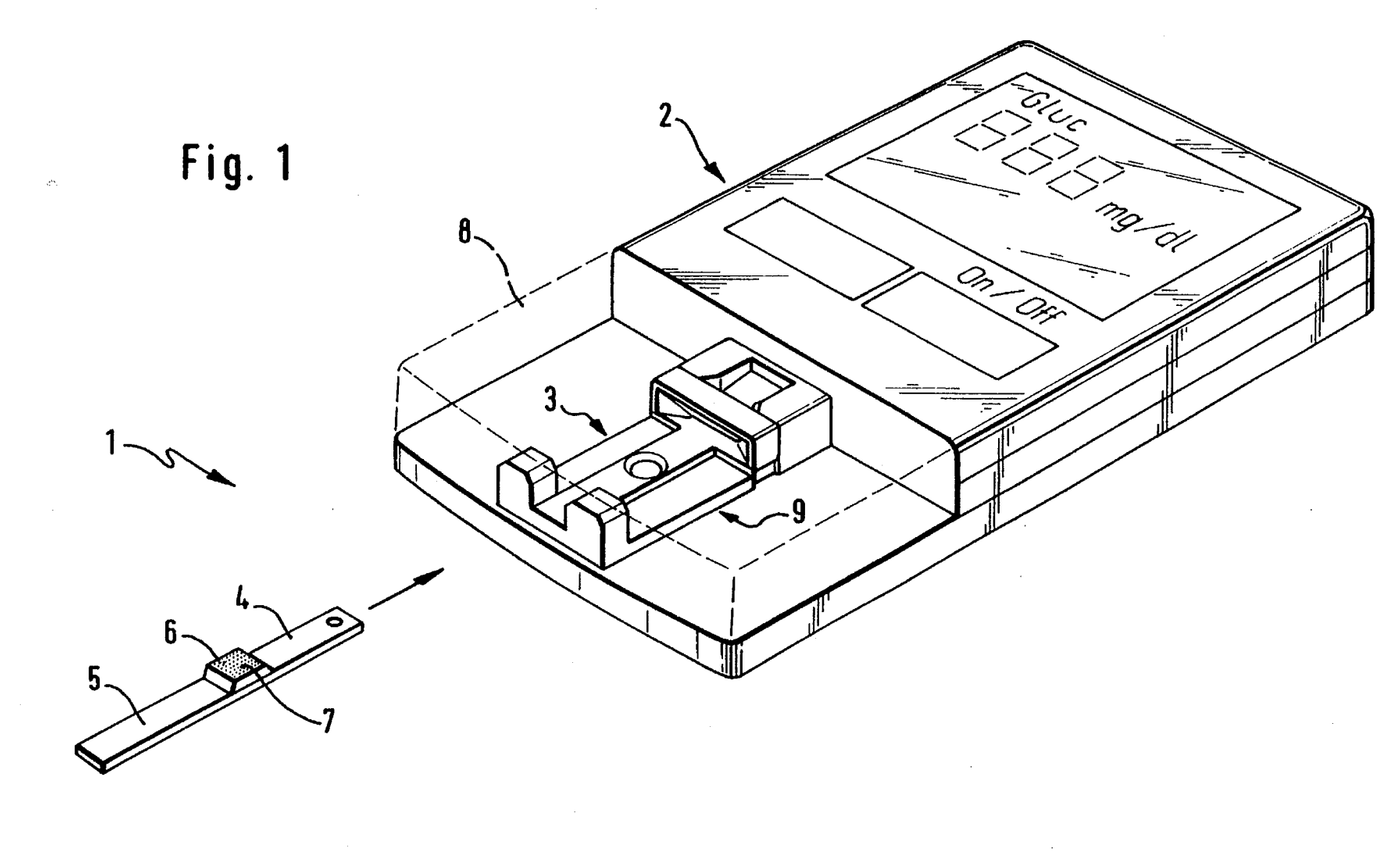
FIG. 1 shows a perspective representation of a test strip analysis system.

FIG. 1 shows a test strip analysis system 1 comprising an evaluation apparatus 2 with a test strip holder 3, and a test strip 4 which can be inserted in said holder. The test strip 4 consists of a base layer 5 and a test layer 6. When body fluid is applied to the test layer 6, chemical reactions take place between the body fluid and the reagents contained in the test layer 6. An optically detectable change resulting from these reactions can be detected by reflection photometry in that part of the test layer 6 which forms the test field 7, and evaluated. In previous test strip analysis systems 1, it was customary to use the opaque flap 8, represented in broken lines, to shield the measurement area 9 from the ambient light which interferes with and falsifies the measurement. In the case of the method according to the invention and the device according to the invention, it is possible to dispense with such a flap 8 without this having an adverse effect to the measurement result.

Figure 2:
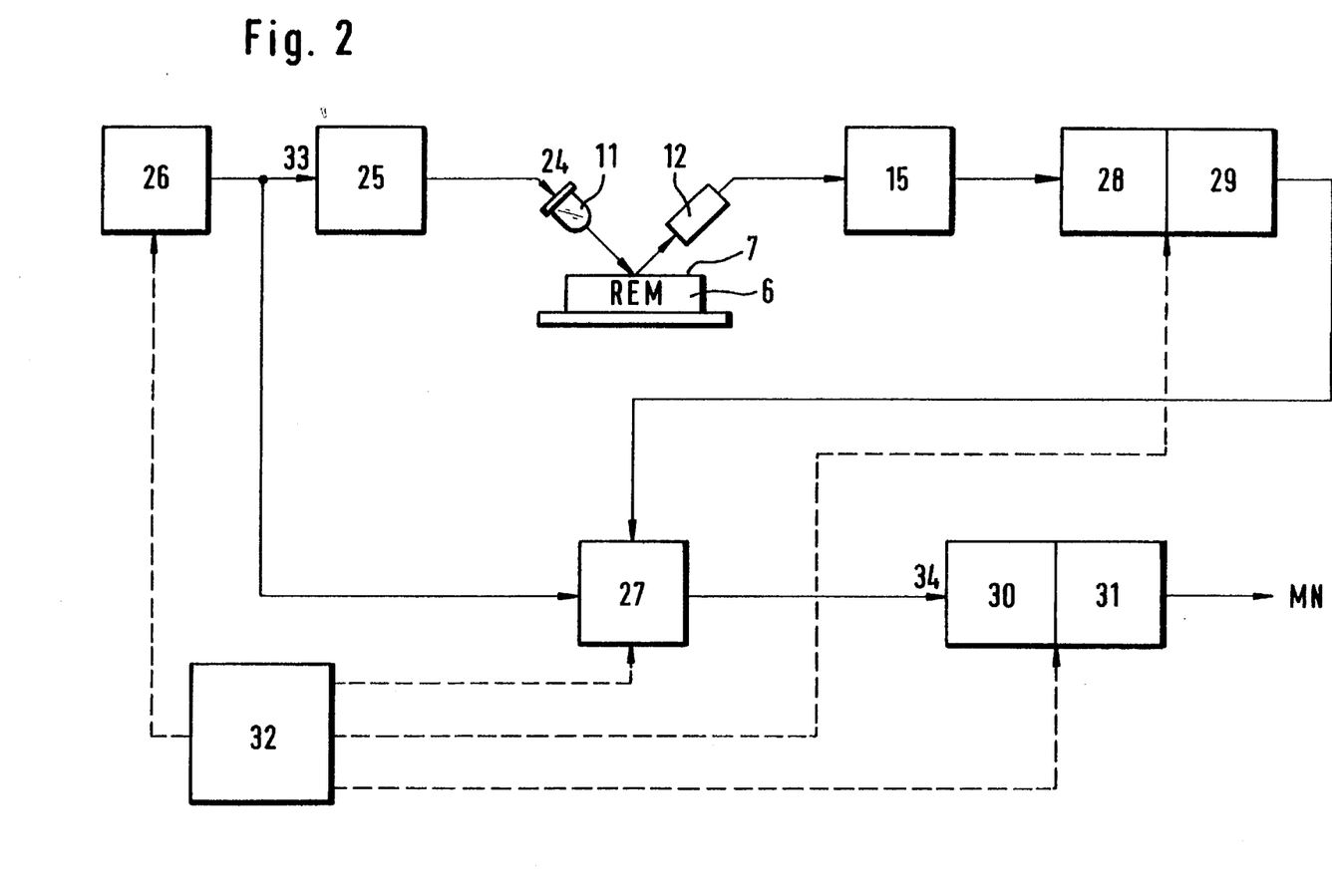
FIG. 2 shows the basic circuit diagram of a preferred circuit arrangement according to the invention.

FIG. 2 shows the basic circuit diagram of a preferred circuit arrangement according to the invention. This has a pulse sequence generator 26, which produces a pseudo-random sequence PZ by means of a retroactive shift register 50 represented in FIG. 4, said sequence serving as a digital reference signal 33 for triggering the clocked light source 11. The pseudo-random sequence PZ is represented in FIG. 5. The light source 11 is a light-emitting diode fed by a triggering device 25, which takes the form of a clocked, controlled constant-current source. The output signal from the triggering device 25, feeding the light source 11, is denoted by 24. The pulse amplitude of the signal 24 is adjustable to match the tolerances and the measurement conditions. The light source 11 irradiates the test field 7, whose reflectance value REM is detected by the measurement receiver 12. The measurement receiver 12 is a photodiode, which converts the reflectance value REM to a photoelectric current.

The preamplifier 15 converts the photoelectric current to a voltage. In the embodiment illustrated, the useful current range is about 1 to 3 mA and the interference current range is about 0 to 10 mA. Saturation of the preamplifier 15 can be evaluated by means of a saturation signal. The signals from the preamplifier 15 are filtered through a high-pass filter 28, which separates out the constant light fraction in order to ensure optimal voltage modulation of the following stages and is preferably located directly after the preamplifier 15.

In the case of DC coupling, the modulation range of the measurement, integration and digitalization circuit would be reduced by the factor by which the interfering signal can exceed the useful signal. This can be avoided by separating out the constant light fraction with the high-pass filter, i.e. by AC coupling of the signals. The lower limiting frequency of the high-pass filter 28 is about 200 Hz and the upper limiting frequency of the preamplifier 15 is about 150 kHz.

Figure 8:
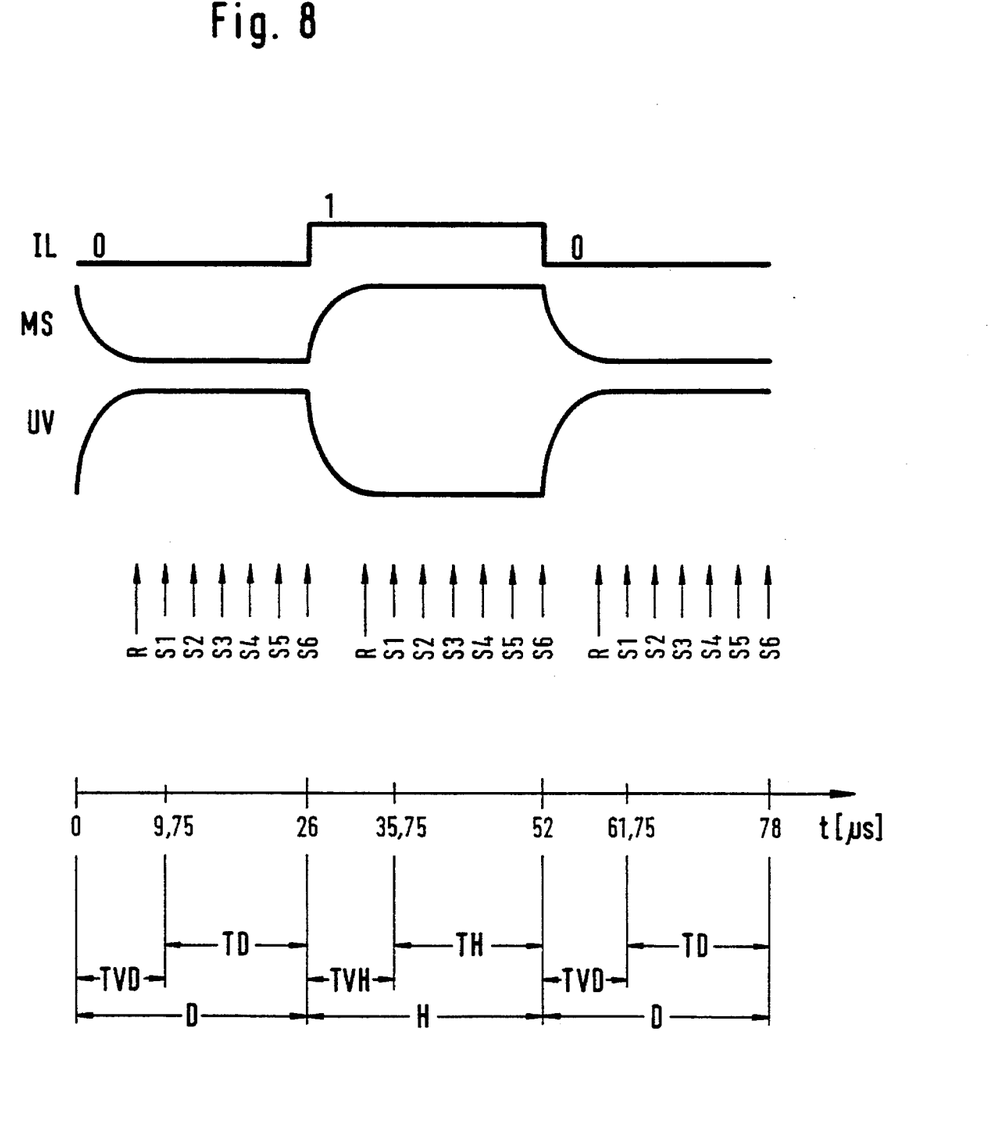
FIG. 8 shows a pulse diagram with the change in the signal forms and sampling points over time.

The transient response of the preamplifier 15 has no effect if, as illustrated in more detail with the aid of FIG. 8, the measurement signal within one bit is in each case determined only after a delay time which is longer than the transient time of the preamplifier 15.

Connected downstream of the high-pass filter 28 is a programmable amplifier 29, whose amplification can be programmed to compensate for the sensitivity tolerances of the light source 11 and the measurement receiver 12, and which ensures a full modulation of the relay multiplication stage 27. The compensation takes place upstream of the relay multiplication stage 27 so as to minimize errors due to its offset voltage drift. The high-pass filter 28 and the programmable amplifier 29 are constructed using switched-capacitor technology so as to maximize integration in the chip. The signals are processed further in the form of sampled capacitor charges with a sampling period of 3.25 µs.

The signals pass into a relay multiplication stage 27, in which the analog signal, in step with the reference signal 33 from the pulse sequence generator 26, is multiplied by +1 over the integrated part of the light phases of the light source 11 and by −1 over the integrated part of the dark phases D. This forms a correlation signal 34 for the subsequent integration, which corresponds to the difference between the analog integrated measured values obtained over the dark phases and the analog integrated measured values obtained over the light phases. The relay multiplication is carried out in the form of six consecutive samples at equal intervals of 3.25 µs within one bit (cycle time of the pseudo-random sequence) of 26 µs. The sampling rate must be high in order to obtain the good properties of the cross-correlation principle, e.g. the high interference suppression, considering the bandwidth of useful and interfering signals. A single sampling within the 26 µs period of the pseudo-random sequence is not sufficient. Although sampling at 1 µs intervals would take into account all the harmonics of the pseudo-random sequence according to FIG. 5, it requires a substantially higher technical expense.

The correlation signal 34 passes into a switchable amplifier 30, also constructed using switched-capacitor technology. The switchable amplification serves to compensate for the tolerances of the light source 11 and of the preamplifier 15. The analog-to-digital converter 31 operates according to the principle of sigma-delta conversion, which enables complete integration of the converter in the chip, such a converter needing only a very small capacitor. It has a resolution of 3844 counts, i.e. about 12 bits, integrates the analog correlation signals 34 over a measurement period of 100 ms and converts them to measurement event numbers MN.

The arrangement according to the invention also has a control circuit 32 for controlling the course of the measurement. The control signals are represented in broken lines.

The measurement signals are monitored at the preamplifier 15, the high-pass filter 28, the programmable amplifier 29, the switchable amplifier 30 and the analog-to-digital converter 31. This enables the test strip analysis system 1 automatically to recognize environmental conditions which do not allow a correct measurement.

The entire circuit is integrated in a chip, only the light source 11 and the measurement receiver 12 being located outside this chip. The chip-internal resistance values and the chip-internal capacitors have relatively high manufacturing tolerances. The tolerances of the preamplifier 15 and of the light source 11 are compensated by means of the changeable amplifications of the programmable amplifier 29 and switchable amplifier 30.

Figure 3:
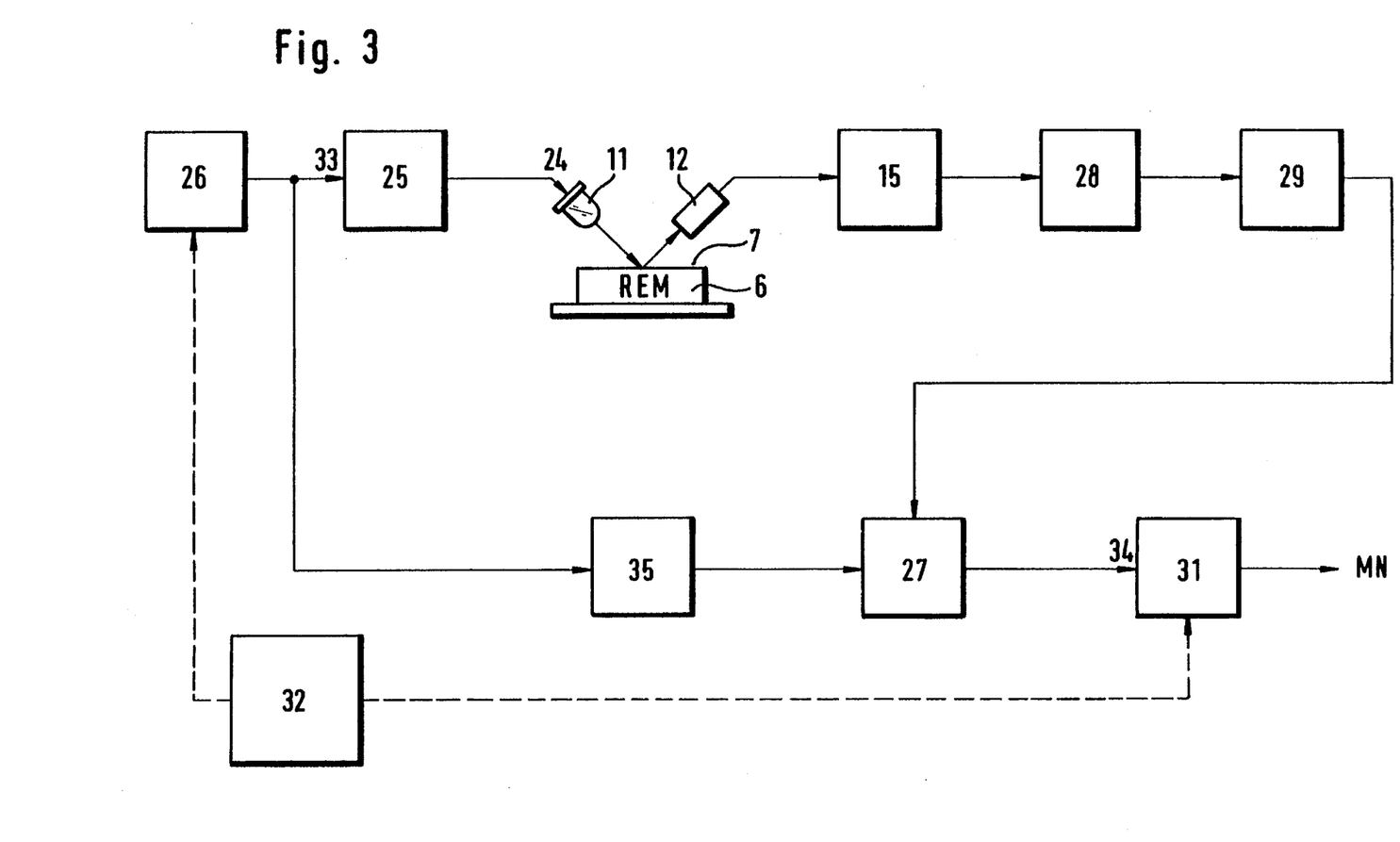
FIG. 3 shows the basic circuit diagram of a modified circuit arrangement according to the invention.

FIG. 3 represents the basic circuit diagram of a modified circuit arrangement according to the invention. Compared with the circuit arrangement represented in FIG. 2, it has the special feature that a delay circuit 35 is provided for the reference signal 33 in order to compensate the group delay time, said circuit ensuring in-phase relay multiplication with the analog signal. As illustrated below with the aid of FIG. 8, it is possible to dispense with compensation of the group delay time if the difference in transit time between the reference signal 33 and the analog measured value, appearing at the relay multiplication stage 27, is smaller than the delay times during which the value from the measurement receiver 12 is not measured at the beginning of each light or dark phase.

Figure 4:
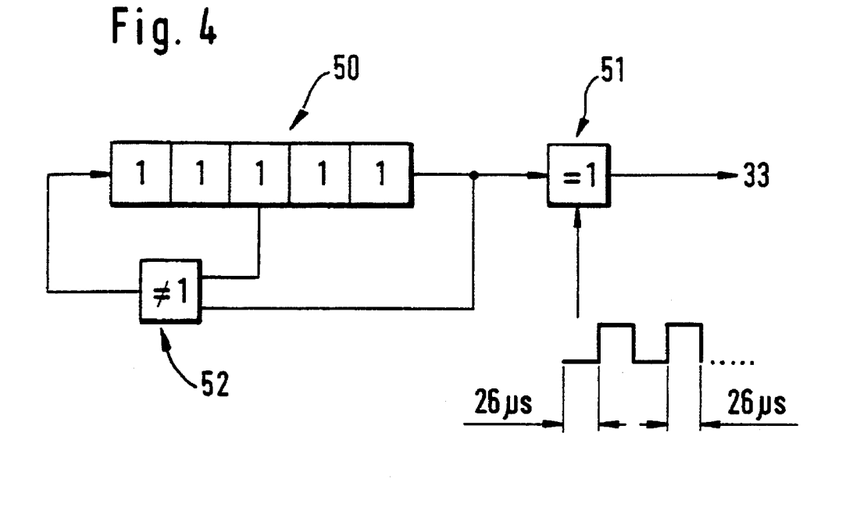
FIG. 4 shows a basic circuit diagram for the production of a pseudo-random sequence with a shift register.
Figure 5:
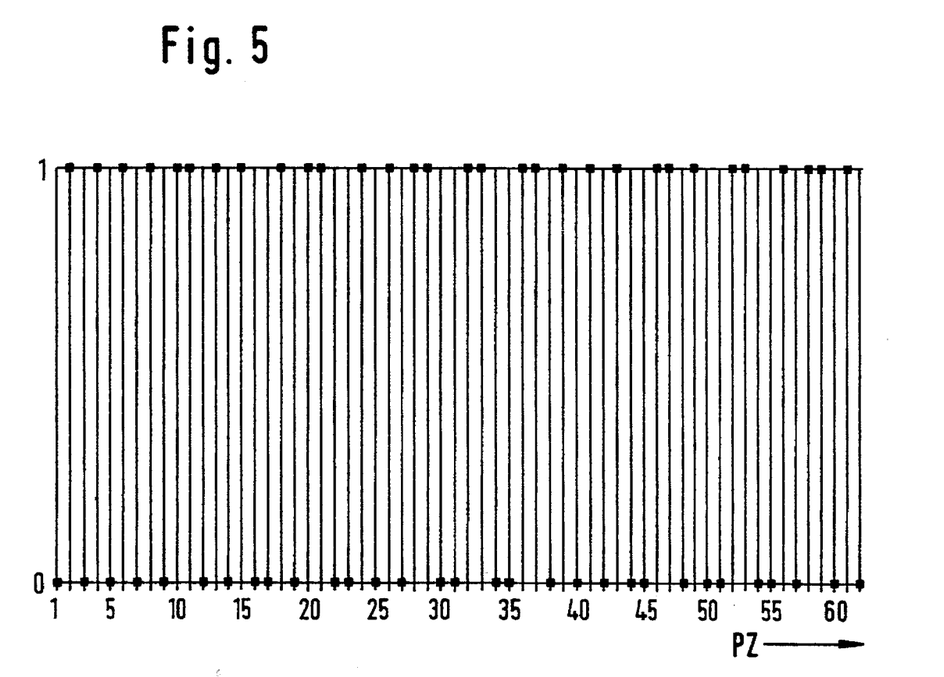
FIG. 5 shows the pseudo-random sequence corresponding to FIG. 4.

FIG. 4 shows the basic circuit diagram for the production of a pseudo-random sequence with a retroactive binary shift register 50 having a length of five. The feedback is effected by tapping the third and fifth registers onto the input via an exclusive OR-gate 52. The five registers are first occupied with ones. These then move one position to the right with every cycle, the logic state supplied at the input being given by the function of the exclusive OR-gate 52. The result in the case represented is a pulse sequence with a maximum of four consecutive identical states (0 or 1). As this has proved unfavorable, a digital modulation is additionally carried out with the aid of the modulator 51, which is an inverse exclusive OR-gate, and the pulse train represented underneath this modulator 51. The cycle of the shift register 50 is 52 ns and the modulation cycle is 26 µs. In consequence the maximum number of identical consecutive states of the digital reference signal 33 is two. Said signal is thus 0 or 1 for a maximum of 52 µs in each case.

FIG. 5 shows a period of the pseudo-random sequence PZ produced by the circuit according to FIG. 4. It is a sequence of 62 bits, each with a pulse length of 26 µs. The pseudo-random sequence PZ is repeated several times during the measurement period in order to give the total integrated value with a sufficient signal-to-noise ratio. In the embodiment illustrated, the 62-bit pseudo-random sequence is repeated 62 times within one measurement period for determining a measurement result, giving a measurement period length of 100 ms. The resulting signal 33 triggers the light source 11 via the triggering device 25 so that said light source irradiates the test field 7 in an irregular sequence of light phases and dark phases, within the measurement period, according to the cycle of the signal 33. Both the light phases and the dark phases have different lengths (only two lengths are possible for each in the Example given), their sequence being irregular.

Figure 6:
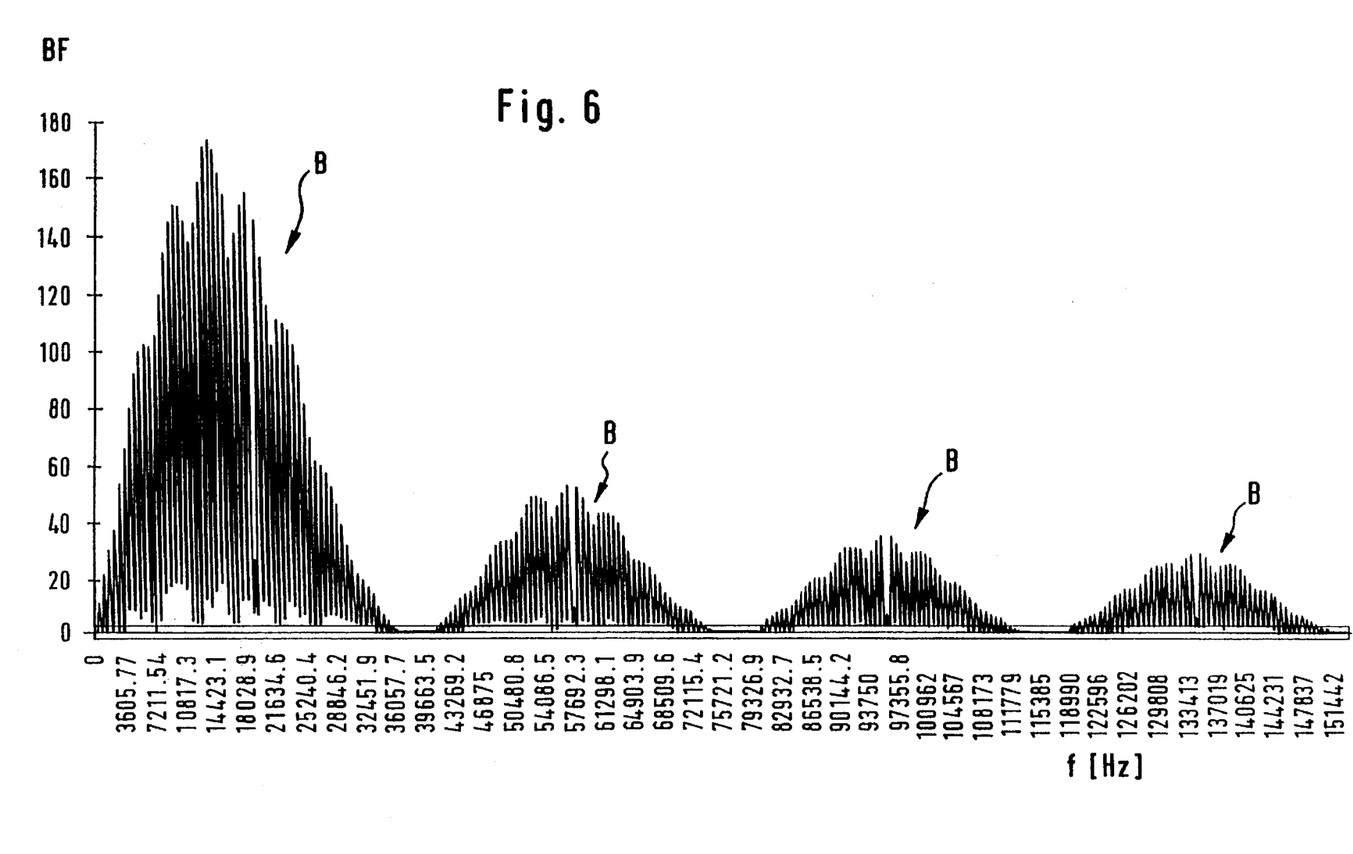
FIG. 6 shows the Fourier-transformed frequency spectrum corresponding to FIG. 5.
Figure 7:
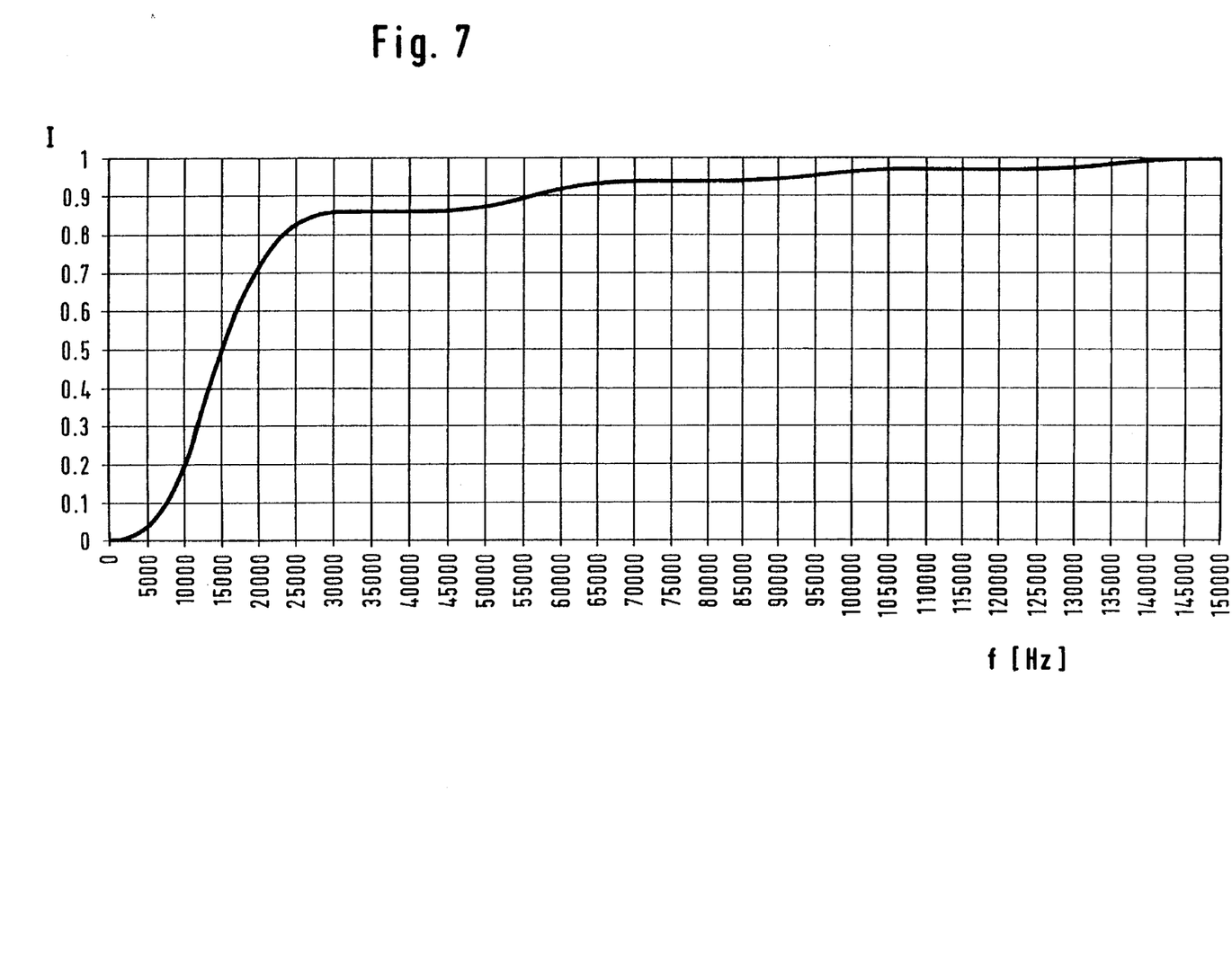
FIG. 7 shows the integrated standardized power density corresponding to FIG. 6.

If four such 62-bit signal sequences are set in succession and a discrete Fourier transformation is then performed according to a cosine window function, the spectrum of FIG. 6 is obtained, showing the magnitude of the frequency amplitudes BF as a function of the frequency f. If the entire pulse sequence of the 100 ms measurement period MP were to be Fourier-transformed, there would be only very slight changes in the shape of this spectrum. The frequency spectrum of the signal 24 feeding the light source 11, obtained by Fourier transformation, ranges from just above zero to about 150 kHz and comprises a large number of frequencies which make a substantial contribution to the overall intensity. The zeros in this spectrum are a consequence of the 52 µs modulation. The integrated standardized power density I corresponding to the frequency spectrum of FIG. 6 is represented in FIG. 7.

As already mentioned, the frequency spectrum should have a substantially uniform distribution. In other words, frequencies which make a substantial contribution to the signal intensity should be present over a broad frequency range; normally—as represented in FIG. 6—the frequencies which make a substantial contribution to the intensity are distributed over several bands B, between which there are frequencies which make a small contribution to the intensity (near zero). Quantitatively, it can be said that frequencies in the frequency spectrum of the signal 24 feeding the light source 11, obtained by Fourier transformation, whose amplitude amounts to more than 5% of the highest amplitude in the entire spectrum should be present over a frequency range whose highest and lowest frequencies differ by a factor of at least 10, preferably by a factor of at least 30 and particularly preferably by a factor of at least 100. This is to be understood as meaning that at least individual frequencies which lie outside this frequency range still have an amplitude of more than 5% of the highest amplitude in the entire spectrum. As regards the absolute limits, it is advantageous if the frequencies which have an amplitude of at least 5% of the highest amplitude in the spectrum are present over a frequency range whose lower limit is below 5 kHz, preferably below 1 kHz, and whose upper limit is above 50 kHz, preferably above 100 kHz. The number of frequencies in the Fourier-transformed frequency spectrum which have an amplitude of at least 5% of the frequency with the highest amplitude in the frequency spectrum should be greater than 20, preferably greater than 50 and particularly preferably greater than 100.

FIG. 8 shows a pulse diagram with the change in the signal forms and sampling points over time. The following are represented as a function of the time t for a dark-light-dark pulse sequence, i.e. for a pulse sequence 0-1-0 of the reference signal 33: the current IL from the triggering device 25 (signal 24) feeding the light source 11; the output signal MS from the preamplifier 15; and the output voltage UV from the programmable amplifier 29, which is inverted relative to MS.

The current IL feeding the light source 11, controlled by the pulse sequence generator 26, has an almost step-like shape, each light and dark cycle having a length of 26 µs. (In the case represented, the sequence 0-1-0 appears regular, but this Figure depicts only a small segment of the measurement period, in which the light and dark phases form an irregular sequence.) Due to overshoot, transient and relaxation effects, the measurement signal from the measurement receiver 12, and hence the signal MS, can follow the abrupt change in the current IL only with finite rise and fall times (about 9.25 µs here). The output voltage UV from the programmable amplifier 29 follows the shape of MS as an inversion.

Times are marked with arrows underneath the signal waveform UV. Numerical values and the notations used below for particular time spans are indicated underneath in FIG. 8.

The integration of the electrical reference of the sigma-delta converter begins at the time R. This time can lie within the rise and fall times of the signal UV, thereby making meaningful use of these times in which the signal UV has not yet reached its correct value and is therefore not to be integrated.

At the times S1, which are later than the beginning of a light phase H or dark phase D by the delay time TVH or TVD of 9.75 µs in each case, the relay multiplication between the reference signal 33 and the analog signal UV is started for six consecutive samples at equal intervals of 3.25 µs. The six samples lie within the periods TD or TH of the dark phase D or light phase H, in which the signal UV has reached its final value and is therefore to be integrated. The light and dark phases are preferably of equal length so that the measurement result of the dark phases can be subtracted from the measurement result of the light phases without a correction factor.

We claim:

1. A method for detecting and evaluating analog photometric signals in a test carrier analysis apparatus, comprising the steps of:

holding a test field of a test carrier in a holder on the analysis apparatus;

irradiating said test field by a light source, said light source being clocked in light and dark phases;

detecting light reflected by the test field, said detecting being conducted by a measurement receiver, said measurement receiver providing measurement signals representing a measured value indicative of the detected light;

evaluating the measured value in a measurement integration and digitalization circuit, said evaluation including the steps of integrating the measured value over at least part of each light phase of a plurality of light phases of a measurement period of said clocking and over at least part of each dark phase of a plurality of dark phases of the measurement period;

forming a total integrated value from integrals of the light phases and dark phases in the evaluation step, wherein the light phases and dark phases within the measurement period form an irregular sequence having a frequency spectrum which comprises a large number of different frequencies.

2. A method for detecting and evaluating analog photometric signals as recited in claim 1, wherein the irregular sequence of light phases and dark phases is generated as a pseudo-random sequence.

3. A method according to claim 2, wherein the measured value from the measurement receiver is integrated over a plurality of identical pseudo-random sequences, in order to form the total integrated value.

4. A method according to claim 1, wherein signals of the measurement receiver are transmitted to the measurement integration and digitalization circuit for the evaluation step through a high-pass filter.

5. A method according to claim 1, wherein the measured value from the measurement receiver is not integrated during a delay time which occurs at the beginning of each light phase and dark phase.

6. A method according to claim 1, further comprising a plurality of consecutive sampling steps to form the total integrated value from the measured value over the measurement period.

7. A method according to claim 1, further comprising the step of providing an integrator as part of the measurement integration and digitalization circuit, applying a measurement signal from the measurement receiver to the integrator, with opposite polarity being applied during the dark phases and during the light phases, wherein an analog integrated measured value obtained during the dark phases is subtracted from the analog integrated measured value obtained during the light phases, to provide a total analog integrated value, wherein the integrated parts of the light phases and the dark phases are of equal size.

8. A method according to claim 7, wherein the integrator converts the integrated value to a digital signal, and operates by a dual-slope method.

9. A method according to claim 7, wherein the integrator converts the integrated value to a digital signal, and operates by a sigma-delta method.

10. A method according to claim 1, wherein frequencies in the frequency spectrum of the irregular sequence of the light phases and dark phases which have an amplitude of at least 5% of a highest amplitude in the frequency spectrum are disposed in a frequency range having a highest and a lowest frequency which differ from each other by a factor of at least 10.

11. A method according to claim 10, wherein said highest and lowest frequencies differ from each other by a factor of at least 30.

12. A method according to claim 10, wherein said highest and lowest frequencies differ from each other by a factor of at least 100.

13. A method according to claim 1, wherein frequencies in the frequency spectrum of the irregular sequence of the light phases and the dark phases which have an amplitude of at least 5% of an amplitude of the frequency which has a highest amplitude in the frequency spectrum are present in a frequency range whose lower limit is below 10 kHz and whose upper limit is above 100 kHz.

14. A method according to claim 13, wherein the frequency range has a lower limit of below 5 kHz and an upper limit of above 50 kHz.

15. A method according to claim 13, wherein the frequency range has a lower limit of below 10 kHz and an upper limit of above 50 kHz.

16. A method according to claim 13, wherein the frequency range has a lower limit of below 5 kHz and an upper limit of above 100 kHz.

17. A method according to claim 1, wherein a number of frequencies in the frequency spectrum of the irregular sequence of the light phases and the dark phases which have an amplitude of at least 5% of an amplitude of a frequency which has a highest amplitude in the frequency spectrum is greater than 20.

18. A method according to claim 17, wherein the number of frequencies is greater than 50.

19. A method according to claim 17, wherein the number of frequencies is greater than 100.

20. An apparatus for detecting and evaluating analog photometric signals, said apparatus comprising:

light source means for irradiating a test field of a test carrier to be examined;

triggering means coupled to said light source means for triggering said light source means, said triggering means triggering said light source means in light-dark phases;

a pulse sequence generator coupled to said triggering means for generating a pulse sequence therefore;

measurement means for detecting and measuring light reflected by the test field, said measurement means comprises a measurement receiver generating measurement signals representing a measured value;

measurement integration and digitalization means coupled to said measurement means, said measurement integration and digitalization means measuring, integrating and digitalizing said measured value, wherein the pulse sequence generator is a random sequence generator generating an irregular pulse sequence.

21. An apparatus according to claim 20, wherein said measurement integration and digitalization means comprises:

preamplifier means for amplifying measurement signals from the measurement means;

relay multiplication means for producing a correlation signal, said relay multiplication means multiplying an output signal from the preamplifier means with opposite polarity for a duration of a measurement period when said measurement means is detecting light reflected by the test field, said output signal being multiplied during at least part of a light phase and at least part of a dark phase of the light source;

an analog-to-digital converter for integrating the correlation signal over a measurement period, wherein a first analog integrated measured value obtained over an integrated part of a dark phase is subtracted from a second analog integrated measured value obtained over an integrated part of a light phase, thereby yielding a total analog integrated value, said analog-to-digital converter also for converting said analog correlation signal to a measurement event number, said measurement integration and digitalization means also including control circuit for controlling a course of the measurement.

22. An apparatus according to claim 21, further comprising a programmable amplifier connected downstream of the preamplifier means, said programmable amplifier for compensating for systematic sensitivity tolerances of the light source means and the measurement means.

23. An apparatus as recited in claim 22, wherein the programmable amplifier comprises switched capacitor technology.

24. An apparatus as recited in claim 22, further comprising a monitoring device which sets an error bit when a saturation of the measurement signals occurs, said monitoring device being connected to the programmable amplifier.

25. An apparatus according to claim 21, further comprising a switchable amplifier for compensating for tolerances of the light source means and the preamplifier means, said switchable amplifier being connected upstream of the analog-to-digital converter.

26. An apparatus as recited in claim 25, wherein the switchable amplifier comprises switched capacitor technology.

27. An apparatus as recited in claim 25, further comprising a monitoring device which sets an error bit when a saturation of the measurement signals occurs, said monitoring device being coupled to the switchable amplifier.

28. An apparatus as recited in claim 21, further comprising a monitoring device which sets an error bit when a saturation of the measurement signals occurs, said monitoring device being connected to the preamplifier means.

29. An apparatus as recited in claim 21, further comprising a monitoring device which sets an error bit when a saturation of the measurement signals occurs, said monitoring device being connected to the analog-to-digital converter.

30. An apparatus as recited in claim 21, wherein the triggering means, the pulse sequence generator, the measurement integration and digitalization means, the preamplifier means, the relay multiplication means and the analog-to-digital converter are integrated in a semiconductor chip.

31. An apparatus according to claim 20, wherein the pulse sequence generator comprises a circuit generating a pseudo-random sequence.

32. An apparatus as recited in claim 20, wherein the pulse sequence generator comprises a binary retroactive shift register for producing a pseudo-random sequence.

33. An apparatus according to claim 32, further comprising a modulator connected downstream of the shift register.

34. An apparatus according to claim 20, wherein the analog-to-digital converter comprises a sigma-delta converter.

35. An apparatus according to claim 20, further comprising a high-pass filter coupled to the measurement means, for filtering the measurement signals therefrom.

36. An apparatus as recited in claim 35, wherein the high-pass filter comprises switched capacitor technology.

37. An apparatus as recited in claim 35, further comprising a monitoring device which sets an error bit when a saturation of the measurement signals occurs, said monitoring device being coupled to the high pass filter.

\* \* \* \* \*